(12) United States Patent
Stahl et al.

(10) Patent No.: US 11,872,063 B2
(45) Date of Patent: *Jan. 16, 2024

(54) SYSTEM AND METHOD FOR DIAGNOSIS AND TREATMENT

(71) Applicant: SHANGHAI UNITED IMAGING HEALTHCARE CO., LTD., Shanghai (CN)

(72) Inventors: Johannes Stahl, Houston, TX (US); Supratik Bose, Houston, TX (US); Li Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 214 days.

This patent is subject to a terminal disclaimer.

(21) Appl. No.: 17/141,207

(22) Filed: Jan. 4, 2021

(65) Prior Publication Data

US 2021/0121140 A1 Apr. 29, 2021

Related U.S. Application Data

(63) Continuation of application No. 16/202,157, filed on Nov. 28, 2018, now Pat. No. 10,881,360, which is a (Continued)

(51) Int. Cl.
*A61B 6/04* (2006.01)
*A61N 5/10* (2006.01)
(Continued)

(52) U.S. Cl.
CPC .......... *A61B 6/0407* (2013.01); *A61B 6/0492* (2013.01); *A61B 6/488* (2013.01);
(Continued)

(58) Field of Classification Search
CPC .......... A61N 5/1069; A61N 2005/1061; A61N 5/1049; A61B 6/032; A61B 6/0407; A61B 6/0492; A61B 6/5276
See application file for complete search history.

(56) References Cited

U.S. PATENT DOCUMENTS 5,613,252 A 3/1997 Yu et al.
6,618,467 B1 * 9/2003 Ruchala ............... A61N 5/1048
378/65
(Continued)

FOREIGN PATENT DOCUMENTS

CN 2529633 Y 1/2003
CN 2873102 Y 2/2007
(Continued)

OTHER PUBLICATIONS

International Search Report in PCT/CN2017/115945 dated Aug. 29, 2018, 4 pages.
(Continued)

*Primary Examiner* — Chih-Cheng Kao
(74) *Attorney, Agent, or Firm* — METIS IP LLC

(57) ABSTRACT

A method for determining a deformation measurement of a couch in a medical procedure may include determining a first deformation measurement of the couch at a reference point, the first deformation measurement corresponding to a first working position of the couch. The method may also include determining a second deformation measurement of the couch at the reference point, the second deformation measurement corresponding to a second working position of the couch. The method may further include determining a difference between the first deformation measurement and the second deformation measurement and causing an adjustment of one of the first working position and the second working position of the couch based on the difference
(Continued)

between the first deformation measurement and the second deformation measurement.

20 Claims, 12 Drawing Sheets

Related U.S. Application Data continuation of application No. PCT/CN2017/115945, filed on Dec. 13, 2017.

(51) Int. Cl.
  *A61B 6/00* (2006.01)
  *A61B 6/03* (2006.01)
(52) U.S. Cl.
  CPC .......... *A61B 6/5276* (2013.01); *A61N 5/1069* (2013.01); *A61B 6/032* (2013.01); *A61N 5/1049* (2013.01); *A61N 2005/1061* (2013.01)

(56) References Cited

U.S. PATENT DOCUMENTS

| | | | |
|---|---|---|---|
| 10,881,360 B2* | 1/2021 | Stahl | .................... A61B 6/488 |
| 2002/0065611 A1* | 5/2002 | Boehm | .................. H04N 5/325 |
| | | | 348/E5.088 |
| 2005/0180544 A1 | 8/2005 | Sauer et al. | |
| 2006/0093093 A1* | 5/2006 | Chao | .................... A61B 6/5276 |
| | | | 378/207 |
| 2007/0297566 A1 | 12/2007 | Urano et al. | |
| 2008/0031414 A1 | 2/2008 | Coppens | |
| 2008/0289106 A1 | 11/2008 | Beyer et al. | |
| 2009/0003522 A1 | 1/2009 | Chien et al. | |
| 2009/0293627 A1 | 12/2009 | Tham et al. | |
| 2010/0067660 A1 | 3/2010 | Maurer, Jr. et al. | |
| 2013/0133247 A1 | 5/2013 | Kerns et al. | |
| 2014/0334608 A1* | 11/2014 | Mulzer | .................... A61B 6/04 |
| | | | 378/207 |
| 2014/0359940 A1 | 12/2014 | Ahlman | |
| 2016/0113610 A1 | 4/2016 | Freudenberger | |
| 2016/0151025 A1 | 6/2016 | Gatayama et al. | |
| 2016/0213951 A1 | 7/2016 | Uhlemann et al. | |
| 2017/0189719 A1 | 7/2017 | Liu et al. | |
| 2017/0189720 A1 | 7/2017 | Liu et al. | |
| 2017/0189724 A1 | 7/2017 | Liu et al. | |
| 2017/0311896 A1* | 11/2017 | Morger | ................. A61B 6/032 |
| 2018/0070004 A1 | 3/2018 | Du | |
| 2018/0300537 A1 | 10/2018 | Qian et al. | |
| 2018/0339172 A1* | 11/2018 | Stahl | .................... A61N 5/1069 |
| 2019/0080459 A1* | 3/2019 | Lachaine | ............. A61N 5/1045 |

FOREIGN PATENT DOCUMENTS

| | | |
|---|---|---|
| CN | 201150544 Y | 11/2008 |
| CN | 201668169 U | 12/2010 |
| FR | 2611490 A1 | 9/1988 |
| JP | 2004180846 A * | 7/2004 |
| WO | 0185085 A2 | 11/2001 |
| WO | 2006083703 A2 | 8/2006 |

OTHER PUBLICATIONS

Written Opinion in PCT/CN2017/115945 dated Aug. 29, 2018, 4 pages.

* cited by examiner

600

| Determining a first deformation measurement of a couch at a reference point, the first sag measurement corresponding to a first working position of the couch | ~602 |

↓

| Determining a second deformation measurement of the couch at the reference point based on at least one first measuring device, the second sag measurement corresponding to a second working position of the couch | ~604 |

↓

| Determining a difference between the first deformation measurement and the second deformation measurement | ~606 |

↓

| Adjusting the second working position of the couch based on the difference between the first deformation measurement and the second deformation measurement | ~608 |

```
Determining a displacement measurement of a
reference point on a couch between a first working      702
position of the couch and a second working position of
the couch by using at least one measuring device
                         │
                         ▼
Determining a deformation measurement of the couch
at the reference point based on the displacement        704
measurement of the couch, the sag measurement of
the couch corresponding to the second working
position
                         │
                         ▼
Adjusting the second working position of the couch      706
based on the deformation measurement of the couch at
the reference point
```

FIG. 7

SYSTEM AND METHOD FOR DIAGNOSIS AND TREATMENT

CROSS REFERENCE TO RELATED APPLICATION

This present application is a continuation of U.S. application Ser. No. 16/202,157 filed on Nov. 28, 2018, which is a continuation of International Application No. PCT/CN2017/115945 filed on Dec. 13, 2017, the entire contents of each of which are incorporated herein by reference.

TECHNICAL FIELD

The present disclosure generally relates to medical diagnosis and treatment system, and more specifically relates to methods and systems for determining a deformation of a couch in a medical procedure.

BACKGROUND

Various imaging techniques have been widely used in medical diagnosis, radiation therapy planning, surgery planning and other medical procedures, such as an X-ray photography, a magnetic resonance imaging (MRI), a computed tomography (CT), a positron emission tomography (PET), etc. Generally, a couch may be used to support and/or transfer a subject to be examined to a scanning region of an imaging device and/or a treatment device. In some embodiments, a couch loaded with the subject (e.g., a patient) may be deformed such as sag or deflection in a medical procedure. For example, in a multi-modality imaging, the couch may sag when the couch is extended along the longitudinal direction of the couch to scanning regions of the multi-modality imaging devices, causing poor image qualities and imprecise fused images. As another example, in an imaging guided radiation therapy (IGRT) procedure, the couch may sag when the couch is moved from an imaging device to a treatment device, causing inaccurate positioning of a target point (e.g., an anatomical point). When the couch moves in a horizontal direction to transfer a subject to a scanning region, the horizontal position of the couch can be read out from a motion control system. However, there are always a certain level of offset or sagging in a vertical direction of the couch that cannot be read out from the motion control system. Thus, it is desirable to provide systems and methods that can correct deformation of the couch in vertical direction to stabilize a spatial position of at least one part of a subject in a medical procedure.

SUMMARY

According to an aspect of the present disclosure, a method for determining a deformation of a couch is provided. The method may be implemented on at least one machine each of which has at least one processor and storage. The method may include determining a first deformation measurement of the couch at a reference point, the first deformation measurement corresponding to a first working position of the couch; determining a second deformation measurement of the couch at the reference point corresponding to a second working position of the couch; determining a difference between the first deformation measurement and the second deformation measurement; and causing an adjustment of one of the first working position and the second working position of the couch based on the difference between the first deformation measurement and the second deformation measurement.

In some embodiments, the first working position of the couch may be related to an imaging position and the second working position of the couch is related to a treatment position.

In some embodiments, the determining a first deformation measurement of the couch at a reference point may include obtaining a first radiation image acquired by an imaging device, the first radiation image including the reference point, the reference point aligning to an isocenter of an imaging device; and determining the first deformation measurement of the couch at the first working position based on the first radiation image acquired by the imaging device.

In some embodiments, the determining the first deformation measurement of the couch at the first working position based on the first radiation image acquired by the imaging device may further include determining first coordinates of the reference point in the first radiation image, the first coordinate of the reference point corresponding to the first deformation measurement of the couch at the reference point; determining second coordinates the reference point in the first radiation image, the second coordinate corresponding to an ideal condition that the couch does not deform; and determining the first deformation measurement of the couch at the first working position based on the first coordinates and the second coordinates.

In some embodiments, the determining a first deformation measurement of the couch at a reference point may include determining a first distance from the reference point on the couch at the first working position to at least one first measuring device by using the at least one first measuring device, the reference point aligning to an isocenter of an imaging device; and determining the first deformation measurement of the couch at the first working distance based on the first distance.

In some embodiments, the at least one first measuring device may include at least one of an optical detector apparatus, a rangefinder apparatus, or an electromagnetic induction apparatus.

In some embodiments, the determining a second deformation measurement of the couch at the reference point may include determining a second distance from the reference point on the couch at the second working position to the at least one first measuring device by using the at least one first measuring device, the reference point aligning to an isocenter of a treatment device; and determining the second deformation measurement of the couch at the second working position based on the second distance.

In some embodiments, the determining a second deformation measurement of the couch at the reference point may include determining a second distance from the reference point on the couch at the second working position to the at least one second measuring device by using the at least one second measuring device, the reference point aligning to an isocenter of a treatment device; and determining the second deformation measurement of the couch at the second working position based on the second distance.

In some embodiments, the determining a second deformation measurement of the couch at the reference point may include obtaining a second radiation image acquired by a detector of a treatment device. The detector is aligned with or angled from a treatment radiation source. The second radiation image may include the reference point, the reference point aligning to an isocenter of the treatment device; and determining the second deformation measurement of the couch at the second working position based on the second radiation image acquired by the treatment device.

In some embodiments, the at least one second measuring device may include at least one of an optical detector apparatus, a rangefinder apparatus, or an electromagnetic induction apparatus.

In some embodiments, the optical detector apparatus may include at least one charge-coupled device (CCD).

In some embodiments, the electromagnetic induction apparatus may include a magnetic induction coil, an electromagnetic launcher (EML), an electromagnetic receiver, the magnetic induction coil being coupled to the couch, etc.

In some embodiments, the rangefinder apparatus may include at least one of an ultrasonic rangefinder, a laser rangefinder, or a radar rangefinder.

According to an aspect of the present disclosure, a method for determining a deformation of a couch is provided. The method may be implemented on at least one machine each of which has at least one processor and storage. The method may include determining a displacement measurement of the couch in a first coordinate direction between a first working position of the couch and a second working position of the couch by using at least one measuring device; determining a deformation measurement of the couch at a reference point based on the displacement measurement of the couch in the first coordinate direction, the deformation measurement of the couch corresponding to the second working position; and causing an adjustment of the second working position of the couch based on the deformation measurement of the couch in the first coordinate direction.

In some embodiments, the at least one measuring device may include at least one of an optical detector apparatus, a rangefinder apparatus, or an electromagnetic induction apparatus.

In some embodiments, the first working position of the couch may be related to an imaging position and the second working position of the couch is related to a treatment position.

According to an aspect of the present disclosure, a system for a medical device is provided. The system may include a computed tomography (CT) device located at a first position, a radio therapy (RT) device located at a second position, the RT device being coupled to the CT device, the CT device and the RT device sharing a same bore, a couch including a movement assembly configured to transfer the couch between the first position and the second position through the bore, and a rangefinder associated with the couch, the rangefinder being configured to acquire data relating to a position of a reference point at the couch. In some embodiments, the CT device may be configured to acquire data relating to a position of a reference point at the couch at the first position. A deformation measurement of the couch at the reference point at the second position relative to the first position may be determined based on the data relating to the position of the reference point at the couch at the second position and the data relating to the position of the reference point at the couch at the first position.

In some embodiments, a first deformation measurement of the couch at the reference point corresponding to the first position may be determined based on based on the data relating to the position of the reference point at the couch at the first position. A second deformation measurement of the couch at the reference point corresponding to the second position may be determined based on the data relating to the position of the reference point at the couch at the second position. The deformation measurement of the couch at the reference point at the second position relative to the first position may be determined based on a difference between the first deformation measurement and the second deformation measurement.

According to an aspect of the present disclosure, a system for determining a deformation of a couch is provided. The system may include a computer-readable storage medium storing executable instructions and at least one processor in communication with the computer-readable storage medium. When the executable instructions are executed, the executable instructions may cause the system to implement a method. The method may include determining a first deformation measurement of the couch at a reference point, the first deformation measurement corresponding to a first working position of the couch; determining a second deformation measurement of the couch at the reference point based on at least one first measuring device, the second deformation measurement corresponding to a second working position of the couch; determining a difference between the first deformation measurement and the second deformation measurement; and causing an adjustment of one of the first working position and the second working position of the couch based on the difference between the first deformation measurement and the second deformation measurement.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include determining a first deformation measurement of the couch at a reference point, the first deformation measurement corresponding to a first working position of the couch; determining a second deformation measurement of the couch at the reference point based on at least one first measuring device, the second deformation measurement corresponding to a second working position of the couch; determining a difference between the first deformation measurement and the second deformation measurement; and causing an adjustment of one of the first working position and the second working position of the couch based on the difference between the first deformation measurement and the second deformation measurement.

According to an aspect of the present disclosure, a system for determining a deformation of a couch is provided. The system may include a data processing module configured to determining a first deformation measurement of the couch at a reference point, the first deformation measurement corresponding to a first working position of the couch; determining a second deformation measurement of the couch at the reference point based on at least one first measuring device, the second deformation measurement corresponding to a second working position of the couch; determining a difference between the first deformation measurement and the second deformation measurement; and causing an adjustment of one of the first working position and the second working position of the couch based on the difference between the first deformation measurement and the second deformation measurement.

According to an aspect of the present disclosure, a system for determining a deformation of a couch is provided. The system may include a computer-readable storage medium storing executable instructions and at least one processor in communication with the computer-readable storage medium. When the executable instructions are executed, the executable instructions may cause the system to implement a method. The method may include determining a displacement measurement of the couch in a first coordinate direction between a first working position of the couch and a second working position of the couch by using at least one measuring device; determining a deformation measurement of the couch at a reference point based on the displacement measurement of the couch in the first coordinate direction, the deformation measurement of the couch corresponding to the second working position; and causing an adjustment of the second working position of the couch based on the deformation measurement of the couch in the first coordinate direction.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include determining a displacement measurement of the couch in a first coordinate direction between a first working position of the couch and a second working position of the couch by using at least one measuring device; determining a deformation measurement of the couch at a reference point based on the displacement measurement of the couch in the first coordinate direction, the deformation measurement of the couch corresponding to the second working position; and causing an adjustment of the second working position of the couch based on the deformation measurement of the couch in the first coordinate direction.

According to an aspect of the present disclosure, a system for determining a deformation of a couch is provided. The system may include a data processing module configured to determining a displacement measurement of the couch in a first coordinate direction between a first working position of the couch and a second working position of the couch by using at least one measuring device; determining a deformation measurement of the couch at a reference point based on the displacement measurement of the couch in the first coordinate direction, the deformation measurement of the couch corresponding to the second working position; and causing an adjustment of the second working position of the couch based on the deformation measurement of the couch in the first coordinate direction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for determining a deformation measurement at a treatment position relative to an imaging position according to some embodiments of the present disclosure;

FIG. 7 is a flowchart illustrating an exemplary process for determining a deformation measurement of a couch at a treatment position relative to an imaging position according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
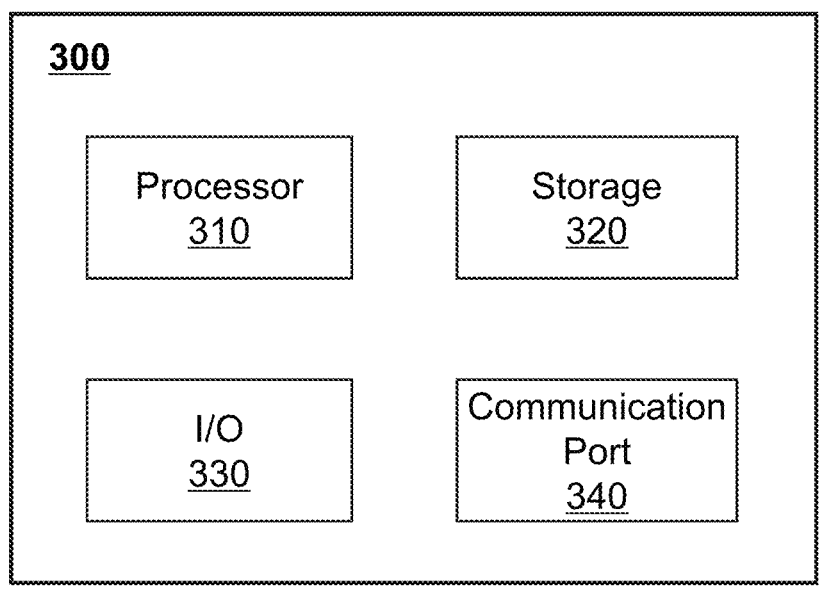
FIG. 3 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical diagnosis and/or treatment. In some embodiments, the medical system may include an diagnosis system. The diagnosis system may include a multi-modality imaging system. The multi-modality imaging system may include, for example, a computed tomography-positron emission tomography (CT-PET) system, a computed tomography-positron emission tomography-magnetic resonance imaging (CT-MRI) system, a X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, or the like, or a combination thereof. In some embodiments, the medical system may include a diagnosis and treatment system. The diagnosis and treatment system may include a treatment plan system (TPS), an image-guide radio therapy (IGRT) system, etc. Merely by way of example, the image guided radio therapy (IGRT) system may include, for example, an CT guided radiotherapy system, an MRI guided radiotherapy system, etc.

The present disclosure relates to a system and method for determining a sag of a couch in a radiotherapy procedure. In some embodiments, a first deformation measurement of the couch at a reference point may be determined. The first deformation measurement of the couch may correspond to an imaging position. A second deformation measurement of the couch at the reference point may be determined. The second deformation measurement of the couch may correspond to a treatment position. Then, a difference between the first deformation measurement and the second deformation measurement may be determined. The difference between the first deformation measurement and the second deformation measurement may be also referred to as a deformation measurement of the couch at the treatment position relative to the imaging position. In some embodiments, the treatment position of the couch may be adjusted based on the difference between the first deformation measurement and the second deformation measurement.

It should be noted that the diagnosis and treatment system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
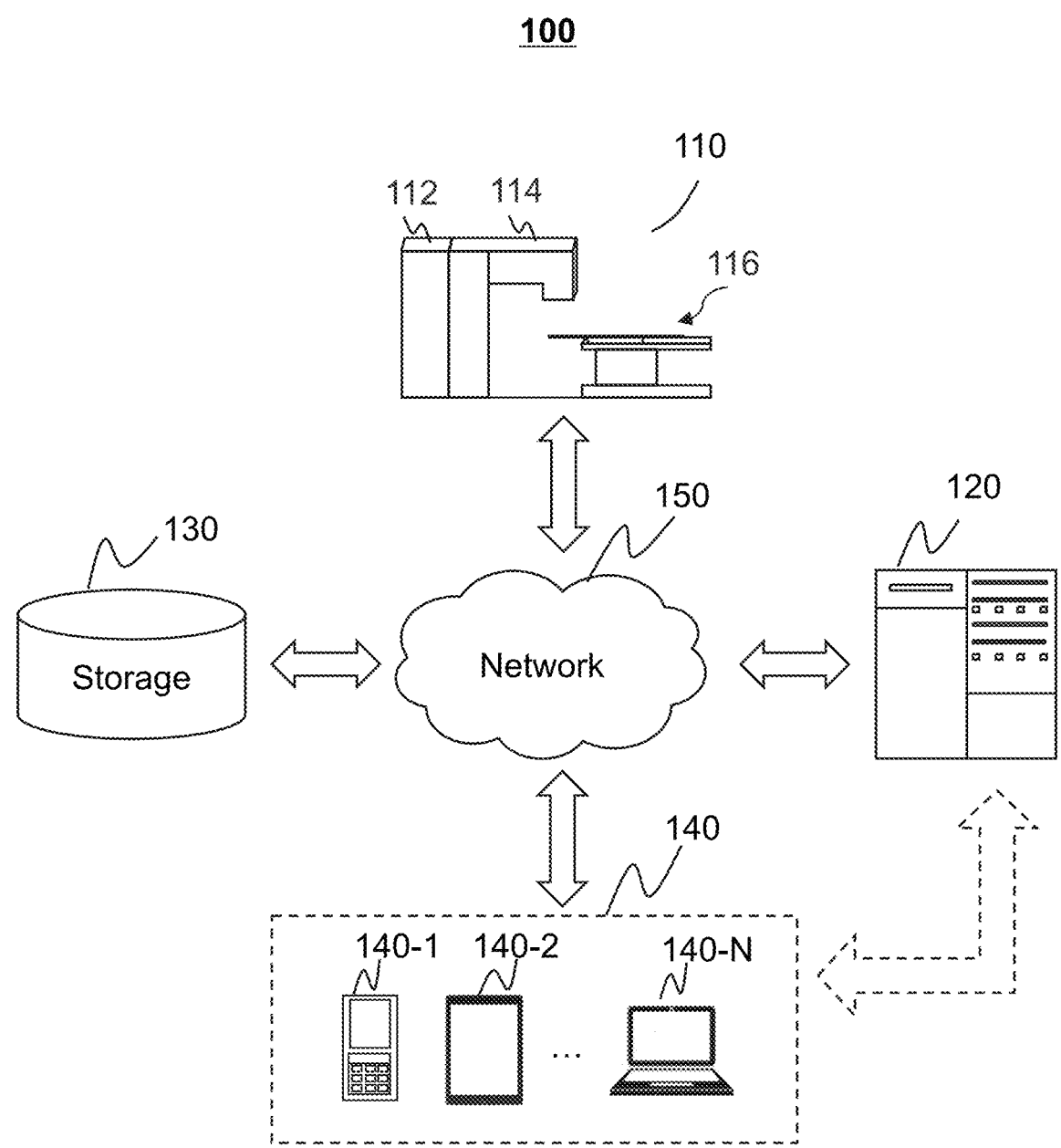
FIG. 1 is a schematic diagram illustrating an exemplary diagnosis and treatment system according to some embodiments of the present disclosure.

FIG. 1 is a schematic diagram illustrating an exemplary diagnosis and treatment system 100 according to some embodiments of the present disclosure. As shown, the diagnosis and treatment system 100 may include an image guided radio therapy (IGRT) apparatus 110, a processing device 120, a storage 130, one or more terminal(s) 140, and a network 150. In some embodiments, the IGRT apparatus 110, the processing device 120, the storage 130, and/or the terminal(s) 140 may be connected to and/or communicate with each other via a wireless connection (e.g., the network 150), a wired connection, or a combination thereof. The connections between the components in the diagnosis and treatment system 100 may vary. Merely by way of example, the IGRT apparatus 110 may be connected to the processing device 120 through the network 150, as illustrated in FIG. 1. As another example, the IGRT apparatus 110 may be connected to the processing device 120 directly. As a further example, the storage 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly.

The IGRT apparatus 110 may be a multi-modality (e.g., two-modality) apparatus to acquire a medical image relating to at least one part of a subject and perform radio therapy on the at least one part of the subject. The medical image may be a computed tomography (CT) image, a magnetic resonance imaging (MRI) image, an ultrasonic image, or the like, or a combination thereof. In some embodiments, the medical image may be a two-dimensional (2D) image, a three-dimensional (3D) image, a four-dimensional (4D) image, or the like, or a combination thereof. The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof.

In some embodiments, the IGRT apparatus 110 may include an imaging device 112, a treatment device 114, and a couch 116. The imaging device 112 may be configured to provide the medical image for determining the at least one part of the subject (e.g., an anatomical point). Exemplary imaging devices may include, for example, a CT device, a cone beam CT device, a PET device, a volume CT device, an MRI device, or the like, or a combination thereof. The treatment device 114 may be configured to perform radio therapy on the at least one part of the subject according to the medical image and other information. Exemplary treatment devices may include a linear accelerator, an X-rays treatment device, etc. The couch 116 may be configured to support and/or transfer the at least one part of the subject to for example, a scanning region of the imaging device 112 and/or the treatment device 114. For example, the couch 116 may be moved to transfer the at least one part of the subject from the imaging device 112 to the treatment device 114.

In some embodiments, the imaging device 112 and the treatment device 114 may be located separately from each other. In some embodiments, the imaging device 112 may be coupled with the treatment device 114. The imaging device 112 and the treatment device 114 may share a same bore which may be used to accommodate a subject to be imaged and/or treated. The couch 116 may be configured to transfer the subject to be imaged and/or treated to a detecting region in the bore. The couch 116 may include a movement assembly configured to move the couch 116 along various directions. For example, the movement assembly may extend the couch 116 along the longitudinal direction of the couch 116. As another example, the movement assembly may lift the couch 116 in the vertical direction. More descriptions of at least one portion of the IGRT apparatus 110 (e.g., the imaging device 112, the treatment device 114, the couch 116) may be found in US Publication No. 20170189719 entitled "RADIATION THERAPY POSITIONING SYSTEM.", US Publication No. 20170189720 entitled "RADIATION THERAPY SYSTEM.", and/or US Publication No. 20170189724 entitled "RADIATION THERAPY SYSTEM.", the contents of which are hereby incorporated by reference. In some embodiments, the IGRT apparatus 110 may further include a measuring device (not shown). The measuring device may be configured to acquire data relating to a position of at least one portion of a component in the IGRT apparatus 110, for example, the couch 116, and/or determine the position of at least one portion of a component of the IGRT apparatus 110, directly. The data relating to a position of at least one portion of a component in the IGRT apparatus 110 may include static data relating to at least one portion of a component in the IGRT apparatus 110, image data relating to at least one portion of a component in the IGRT apparatus 110, or the like, or a combination thereof. Exemplary static data relating to at least one portion of a component in the IGRT apparatus 110 may include a distance from a point on the at least one portion of a component (e.g., the couch 116) of the IGRT apparatus 110 to the measuring device, a direction of the point on the at least one portion of a component in the IGRT apparatus 110 (e.g., the couch 116) relative to the measuring device, etc. Exemplary image data relating to at least one portion of a component of the IGRT apparatus 110 may include an optical image relating to the at least one portion of a component in the IGRT apparatus 110 (e.g., the couch 116), or the like, or a combination thereof. More descriptions of the measuring device may be found in FIG. 2.

The processing device 120 may process data and/or information obtained from the IGRT apparatus 110, the storage 130, and/or the terminal(s) 140. For example, the processing device 120 may reconstruct an image relating to at least one part of a subject (e.g., a tumor) based on projection data collected by the IGRT apparatus 110 (e.g., the imaging device 112). As another example, the processing device 120 may determine a treatment plan based on at least one part of a subject (e.g., a tumor) represented in an image acquired by the imaging device 112. As still an example, the processing device 120 may determine a deformation (e.g., sag) measurement of a couch at a point based on a position of at least one portion of a component of the IGRT apparatus 110 (e.g., the couch 116) and/or data relating to the position of the at least one portion of the component of the IGRT apparatus 110 (e.g., the couch 116) acquired by the measuring device.

In some embodiments, the processing device 120 may be a single server or a server group. The server group may be centralized or distributed. In some embodiments, the processing device 120 may be local or remote. For example, the processing device 120 may access information and/or data from the IGRT apparatus 110, the storage 130, and/or the terminal(s) 140 via the network 150. As another example, the processing device 120 may be directly connected to the IGRT apparatus 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a mobile device 400 having one or more components as described in connection with FIG. 2.

The storage 130 may store data, instructions, and/or any other information. In some embodiments, the storage 130 may store data obtained from the IGRT apparatus 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc.

Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the diagnosis and treatment system 100 (e.g., the processing device 120, the terminal(s) 140, etc.). One or more components in the diagnosis and treatment system 100 may access the data or instructions stored in the storage 130 via the network 150. In some embodiments, the storage 130 may be part of the processing device 120.

The terminal(s) 140 may be connected to and/or communicate with the IGRT apparatus 110, the processing device 120, and/or the storage 130. For example, the terminal(s) 140 may obtain a processed image from the processing device 120. As another example, the terminal(s) 140 may obtain image data acquired via the IGRT apparatus 110 and transmit the image data to the processing device 120 to be processed. In some embodiments, the terminal(s) 140 may include a mobile device 140-1, a tablet computer 140-2, . . ., a laptop computer 140-N, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the diagnosis and treatment system 100. In some embodiments, one or more components of the diagnosis and treatment system 100 (e.g., the IGRT apparatus 110, the processing device 120, the storage 130, the terminal(s) 140, etc.) may communicate information and/or data with one or more other components of the diagnosis and treatment system 100 via the network 150. For example, the processing device 120 may obtain image data from the IGRT apparatus 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the diagnosis and treatment system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
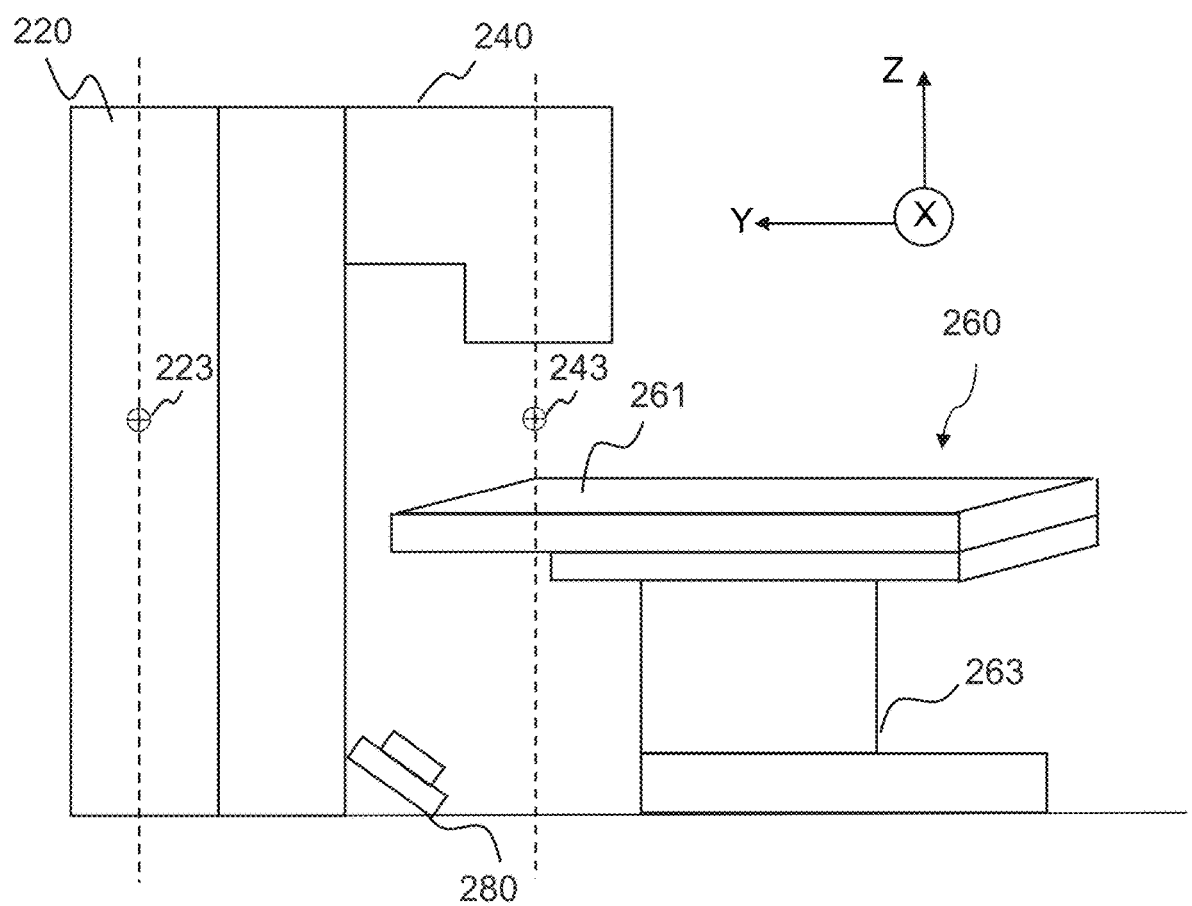
FIG. 2 illustrates a side view of an exemplary RT-CT apparatus and associated components according to some embodiments of the present disclosure.

FIG. 2 illustrates a side view of an exemplary RT-CT apparatus 200 and associated components according to some embodiments of the present disclosure. The RT-CT apparatus 200 may be the exemplary IGRT apparatus 110 as shown in FIG. 1. The RT-CT apparatus 200 may include a CT device 220, an RT device 240, a couch 260, and a measuring device 280.

The CT device 220 may acquire a CT image relating to at least one part of a subject via scanning the at least one part of the subject. In some embodiments, the CT device 220 may include a radiation source, a detector, etc. The radiation source, for example, a tube may emit radiation beams. The detector may detect the radiation beams emitted from the radiation source and generate signals (e.g., electronic signals, digital signals, etc.). The CT image may be generated based on the signals (e.g., electronic signals, digital signals, etc.). In some embodiments, the CT image may be used to identify the at least one part of the subject, classify the at least one part of the subject, diagnosis the at least one part of the subject, determine a spatial position of the at least one part of the subject, etc. The CT device 220 may have an isocenter 223. As used herein, the isocenter 223 of the CT device 220 may refer to an intersection of a rotation axis of the CT device 220, a rotation axis of a radiation source of the CT device 220, and a rotation axis of the couch 260.

The RT device 240 may be used for treatment, for example, performing a radio therapy on the at least one part of the subject determined based on the CT image. The RT device 240 may include a cyclotron, an induction accelerator, a linear accelerator (LINAC), etc. In some embodiments, the CT device 220 and the RT device 240 may be set back to back or adjacent to each other as illustrated in FIG. 2. The CT device 220 and the RT device 240 may have a same rotation axis. Specifically, the CT device 220 may be connected to the RT device 240. In some embodiments, the CT device 220 and the RT device 240 may be set separately from each other. In some embodiments, the CT device 220 and the RT device 240 may be mounted and/or fixed on the ground. In some embodiments, the CT device 220 and/or the RT device 240 may be moveable. For example, the CT device 220 and/or the RT device 240 may be moved using a moveable device (e.g., a trolley or wheels) mounted on the CT device 220 and/or the RT device 240. The RT device 240 may have an isocenter 243. As used herein, the isocenter 243 of the RT device 240 may refer to an intersection of a rotation axis of the RT device 240, a rotation axis of a radiation source of the RT device 240, and a rotation axis of the couch 260.

The couch 260 may be configured to support and/or transfer the at least one part of the subject. The couch 260 may include a table top 261 and a supporting assembly 263. The supporting assembly 263 may support the table top 261. The couch 260 may move in any direction. For example, a longitudinal direction (i.e., along a long axis of table top 261 in the plane of the table top 261 at its retracted configuration), a lateral direction (i.e., along a short axis of the table top 261 in the plane of the table top 261 at its retracted configuration), or a direction oblique to the longitudinal direction and/or the lateral direction. The movement of the couch 260 may be driven manually or by, for example, a motor. In some embodiments, the couch 260 may be moved using a moveable device (e.g., a trolley or wheels) mounted on the couch 260. In some embodiments, the longitudinal direction may be described as Y direction. The lateral direction may be described as the X direction. The X direction and the Y direction are within the plane containing a radiotherapy source of the CT device 220 or the RT device 240 and a rotation center of the RT device 240 and the CT device 220.

In some embodiments, the couch 260 may be used to support a subject in a radiation therapy using a RT device (e.g., the RT 240). In some embodiments, the couch 350 may be used to support a subject in an imaging process using a CT device (e.g., the CT device 220). In some embodiments, a CT device and an RT device may share the same couch 260. A subject supported on the couch 260 may go through both a CT scanning and a radiation therapy by moving the couch 260 from an imaging position to a treatment position, during which the subject does not need to change to from one couch to a different couch.

The measuring device 280 may be configured to collect data relating to a position of the at least one portion of the component (e.g., the couch 260, etc.) and/or a position of at least one portion of a component (e.g., the couch 260, etc.) of the RT-CT apparatus 200, directly. The data relating to a position of at least one portion of a component in the RT-CT apparatus 200 may be used to estimate a position of the least one portion of the component in the RT-CT apparatus 200. The data relating to a position of at least one portion of a component (e.g., the couch 260, etc.) in the RT-CT apparatus 200 may include static data, image data (e.g., an image), or other data relating to a position of at least one portion of a component (e.g., the couch 260, etc.) of the RT-CT apparatus 200 as described elsewhere in the present disclosure. See, for example, FIG. 1 and description thereof.

The measuring device 280 may include at least one of an optical detector apparatus, a rangefinder apparatus, an electromagnetic induction apparatus, or the like, or a combination thereof. Exemplary optical detector apparatus may include one or more photodetectors (e.g., a charge coupled device (CCD)). The optical detector apparatus may include a plurality of photodetectors. The plurality of photodetectors may be arranged as a photodetector lattice. The photodetector lattice may be one-dimensional, two-dimensional (2D), three-dimensional (3D), etc. In some embodiments, the optical detector apparatus may acquire an image relating to a specified region of at least one portion of a component (e.g., the couch 260, etc.) in the RT-CT apparatus 200. For example, the image may relate to a specified region including a reference point on the bottom of the couch 260. The reference point on the bottom of the couch 260 may be aligned with the isocentor 223 of the CT device 220 and/or the isocenter 243 of the RT device 240. Exemplary rangefinder apparatuses may include an ultrasonic rangefinder, a laser rangefinder, a radar rangefinder, etc. The rangefinder apparatuses may be configured to determine a distance and/or a direction from a reference point on the couch to a rangefinder apparatus. Exemplary electromagnetic induction apparatuses may include a magnetic induction coil, an electromagnetic launcher (EML), an electromagnetic receiver, etc. In some embodiments, the magnetic induction coil may be coupled with the couch 260. The electromagnetic launcher (EML) may generate a magnetic field. The magnetic induction coil may generate an electromagnetic signal including movement information relating to the couch 260 when the couch 260 is moved in the magnetic field. The electromagnetic signal including the movement information relating to the couch 260 may be received by the electromagnetic receiver.

In some embodiments, the measuring device 280 may include a first measuring device and a second measuring device. In some embodiments, the first measuring device and the second measuring device may be applied to the CT device 220 and the RT device 240, respectively. For example, the first measuring device may be used to determine a first sag measurement of the couch 260 at an imaging position where the CT device 220 is located. The second measuring device may be used to determine a second sag measurement of the couch 260 at a treatment position where the RT device 240 is located. In some embodiments, the first measuring device and/or the second measuring device may be both applied to the RT device 240 and/or the CT device 220. For example, the first measuring device and the second measuring device may be used to determine the first sag measurement and/or the second sag measurement cooperatively. The first measuring device may be same with or different from the second measuring device.

The measuring device 280 may be disposed at a suitable position in the space accommodating the RT-CT apparatus 200. In some embodiments, the measuring device 280 may be coupled to the CT device 220 and/or the RT device 240. For example, the first measuring device may be coupled to a base of the CT device 220, and/or the second measuring device may be coupled to a base of the RT device 240. In some embodiments, the measuring device 280 may be coupled to the couch 260. For example, a rangefinder apparatus may be coupled to a specified region on the couch. In some embodiments, the measuring device 280 may be disposed relative to the CT device 220, the RT device 240, and/or the couch 260. For example, the measuring device 280 may be mounted on the ground below the couch 260. As another example, the measuring device 280 may be mounted on the ceiling above the couch 260. As still an example, the measuring device 280 may be mounted on an auxiliary supporting device to be parallel with the table top 261 of the couch 260. In some embodiments, the measuring device 280 may be arranged to be aligned with the isocenter 223 of the CT device 220 or the isocenter 243 of the RT device 240. In some embodiments, the measuring device 280 may be arranged with an offset relative to the isocenter 223 of the CT device 220 or the isocenter 243 of the RT device 240.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the RT-CT apparatus 200 may further include an imaging device, such as a PET device, an MRI device, etc. As another example, the measuring device 280 may include one or more sensors (e.g., a speed sensor, a displacement sensor, an accelerator sensor, etc.). The one or more sensors may be configured to collect data relating to a position of at least one portion of a component in the RT-CT apparatus 200.

FIG. 3 is a schematic diagram illustrating exemplary hardware and/or software components of an exemplary computing device 300 on which the processing device 120 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data obtained from the IGRT apparatus 110, the storage 130, terminal(s) 140, and/or any other component of the diagnosis and treatment system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the IGRT apparatus 110, the storage 130, the terminal (s) 140, and/or any other component of the diagnosis and treatment system 100. In some embodiments, the storage 320 may include a mass storage, a removable storage, a volatile read-and-write memory, a read-only memory (ROM), or the like, or a combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for determining a target flip angle schedule.

The I/O 330 may input and/or output signals, data, information, etc. In some embodiments, the I/O 330 may enable a user interaction with the processing device 120. In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 120) to facilitate data communications. The communication port 340 may establish connections between the processing device 120 and the IGRT apparatus 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
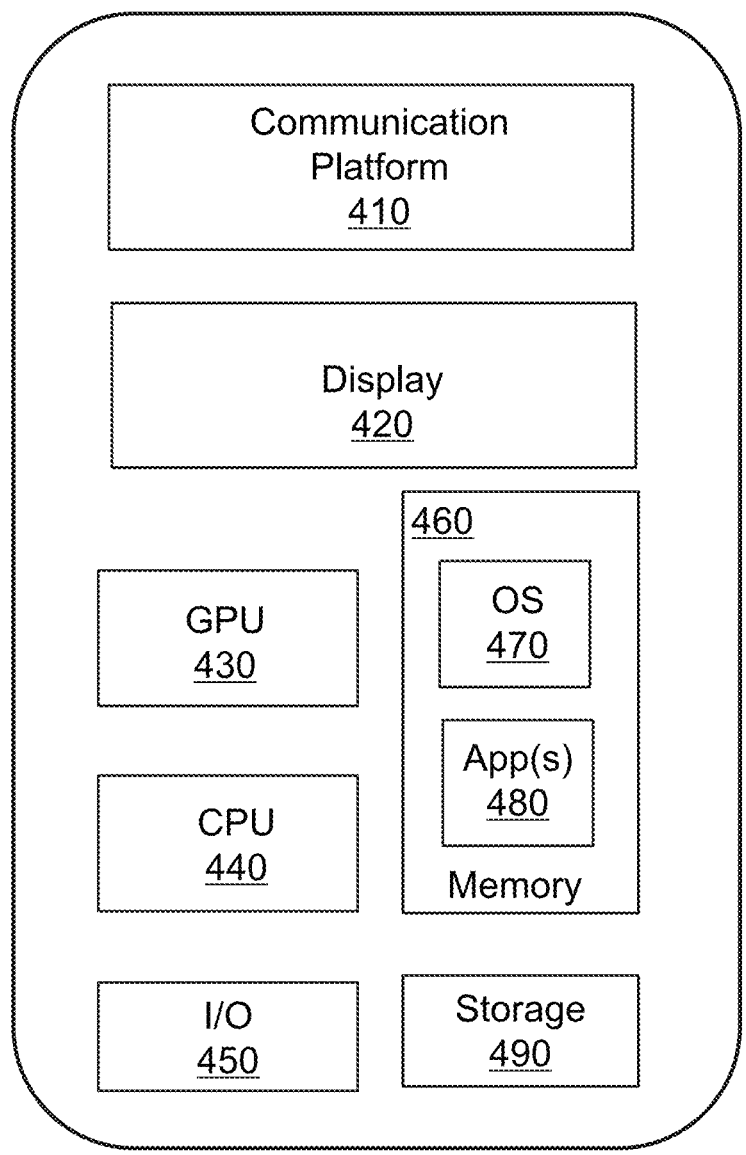
FIG. 4 is a schematic diagram illustrating exemplary hardware and/or software components of an exemplary mobile device on which the terminal(s) may be implemented according to some embodiments of the present disclosure.

FIG. 4 is a schematic diagram illustrating exemplary hardware and/or software components of an exemplary mobile device 400 on which the terminal(s) 140 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the diagnosis and treatment system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
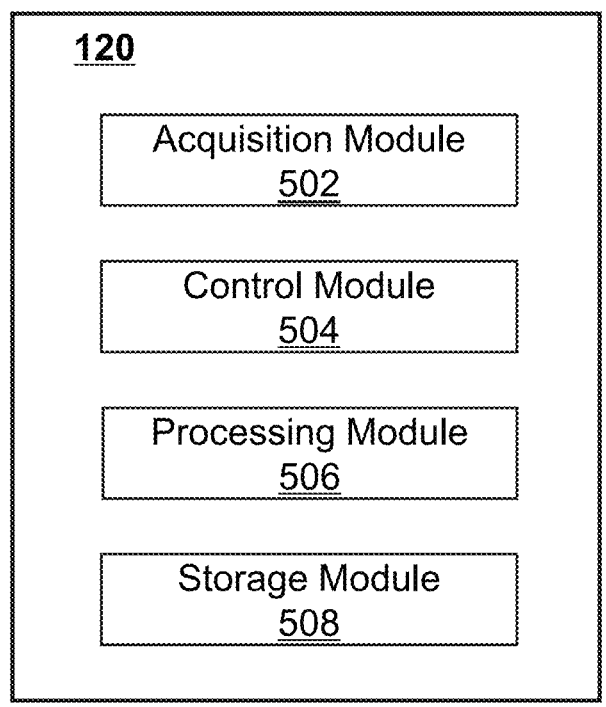
FIG. 5 is a block diagram illustrating an exemplary processing device according to some embodiments of the present disclosure.

FIG. 5 is a block diagram illustrating an exemplary processing device 120 according to some embodiments of the present disclosure. The processing device 120 may include an acquisition module 502, a control module 504, a processing module 506, and a storage module 508. At least a portion of the processing device 120 may be implemented on a computing device as illustrated in FIG. 3 or a mobile device as illustrated in FIG. 4.

The acquisition module 502 may acquire data. In some embodiments, the data may be acquired from the IGRT apparatus 110, the storage 130, and/or the terminal(s) 140. In some embodiments, the data may include image data (e.g., a radiological image, an optical image, etc.), motion or position data (e.g., a speed, a displacement, a distance, an acceleration, etc.) relating to a component in the IGRT apparatus 110, instructions, or the like, or a combination thereof. The instructions may be executed by the processor(s) of the processing device 120 to perform exemplary methods described in the present disclosure. In some embodiments, the acquired data may be transmitted to the processing module 506 for further processing, or stored in the storage module 508.

The control module 504 may control operations of the acquisition module 502, the processing module 506, and/or the storage module 508, for example, by generating one or more control parameters. For example, the control module 504 may control the acquisition module 502 to acquire image data (e.g., a radiological image, etc.) from the imaging device 112 of the IGRT apparatus 110 and/or data relating to position of the couch 116 from the measuring device 280. As another example, the control module 504 may control the processing module 506 to determine a deformation (e.g., sag) measurement of the couch 116 at a reference point when the couch is at an imaging position and/or a treatment position. As a further example, the control module 504 may control the movement of the couch 116 based on a sag measurement of the couch 116 at a reference point when the couch is at a treatment position. In some embodiments, the control module 504 may receive a real-time command or retrieve a predetermined instruction provided by a user (e.g., a doctor) to control one or more operations of the acquisition module 502 and/or the processing module 506. For example, the control module 504 may adjust the acquisition module 502 and/or the processing module 506 to generate image data (e.g., an image) according to the real-time instruction and/or the predetermined instruction. In some embodiments, the control module 504 may communicate with one or more other modules of the processing device 120 for exchanging information and/or data.

The processing module 506 may process data provided by various modules of the processing device 120. In some embodiments, the processing module 506 may process a radiological image relating to at least one part of a subject to determine a sag measurement of the couch 116 at a reference point when the couch 116 is at an imaging position. In some embodiments, the processing module 506 may determine a sag measurement of the couch 116 at a reference point when the couch 116 is at a treatment position based on data relating to a motion or position of the couch 116 collected by the measuring device 280.

The storage module 508 may store information. The information may include programs, software, algorithms, data, text, number, images and some other information. For example, the information may include image data (e.g., a radiological image, an optical image, etc.), motion or position data (e.g., a speed, a displacement, an acceleration, a spatial position, etc.) relating to a component in the IGRT apparatus 110 (e.g., the couch 116), instructions, or the like, or a combination thereof. In some embodiments, the storage module 508 may store program(s) and/or instruction(s) that can be executed by the processor(s) of the processing device 120 to acquire data, determine a spatial position of at least one part of a subject.

In some embodiments, one or more modules illustrated in FIG. 5 may be implemented in at least part of the diagnosis and treatment system 100 as illustrated in FIG. 1. For example, the acquisition module 502, the control module 504, the processing module 506, and/or the storage module 508 may be integrated into a console (not shown). Via the console, a user may set parameters for scanning a subject, controlling imaging processes, controlling parameters for reconstruction of an image, etc. In some embodiments, the console may be implemented via the processing device 120 and/or the terminal(s) 140.

FIG. 6 is a flowchart illustrating an exemplary process 600 for determining a deformation measurement at a treatment position relative to an imaging position according to some embodiments of the present disclosure. In some embodiments, one or more operations of process 600 illustrated in FIG. 6 may be implemented in the diagnosis and treatment system 100 illustrated in FIG. 1. For example, the process 600 illustrated in FIG. 6 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

Figure 9:
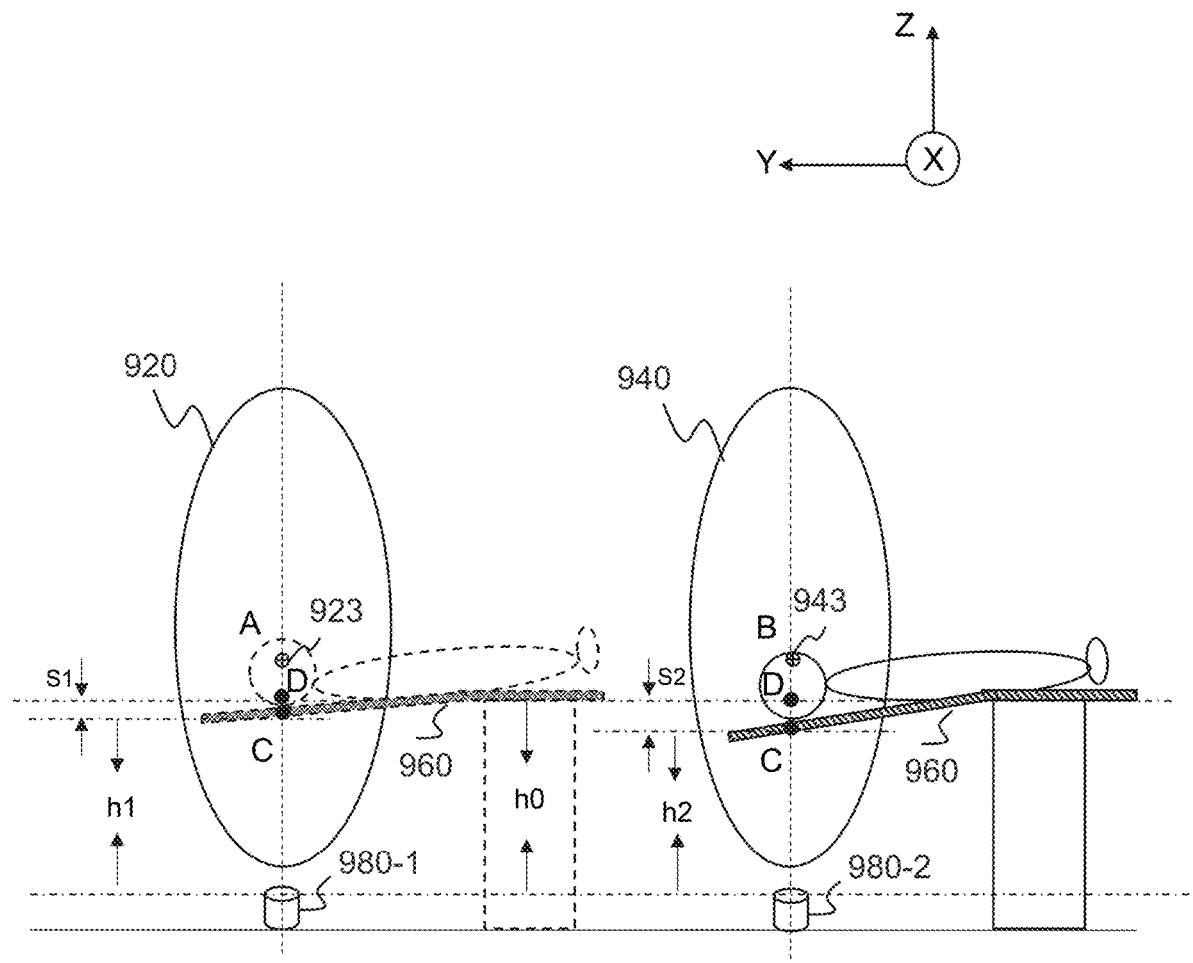
FIG. 9 is a schematic diagram illustrating an example for determining a sag measurement at a treatment position relative to an imaging position according to some embodiments of the present disclosure.

In 602, a first deformation measurement of a couch at a reference point may be determined. The first deformation measurement of the couch may correspond to a first working position of the couch. Operation 602 may be performed by the processing module 506. The first working position of the couch may be refer to an imaging position where an imaging device (e.g., the imaging device 920) is located. The reference point (e.g., point C as shown in FIG. 9) on the couch may be aligned with an isocenter of the imaging device (e.g., the isocenter 923 of the imaging device 920) in a vertical direction when the couch is at the first working position. The first deformation measurement of the couch at the reference point may relate to a position change of the reference point due to carrying a subject and/or the weight of the couch comparing to an ideal condition where the couch does not sag. For example, the first deformation measurement of the couch may include a first sag measurement. Further, the first sag measurement of the couch at the reference point may be determined based on a position change of the reference point in a vertical direction (e.g., the sag measurement S1 as shown in FIG. 9) due to carrying a subject and/or the weight of the couch comparing to an ideal condition when the couch does not sag.

Figure 8:
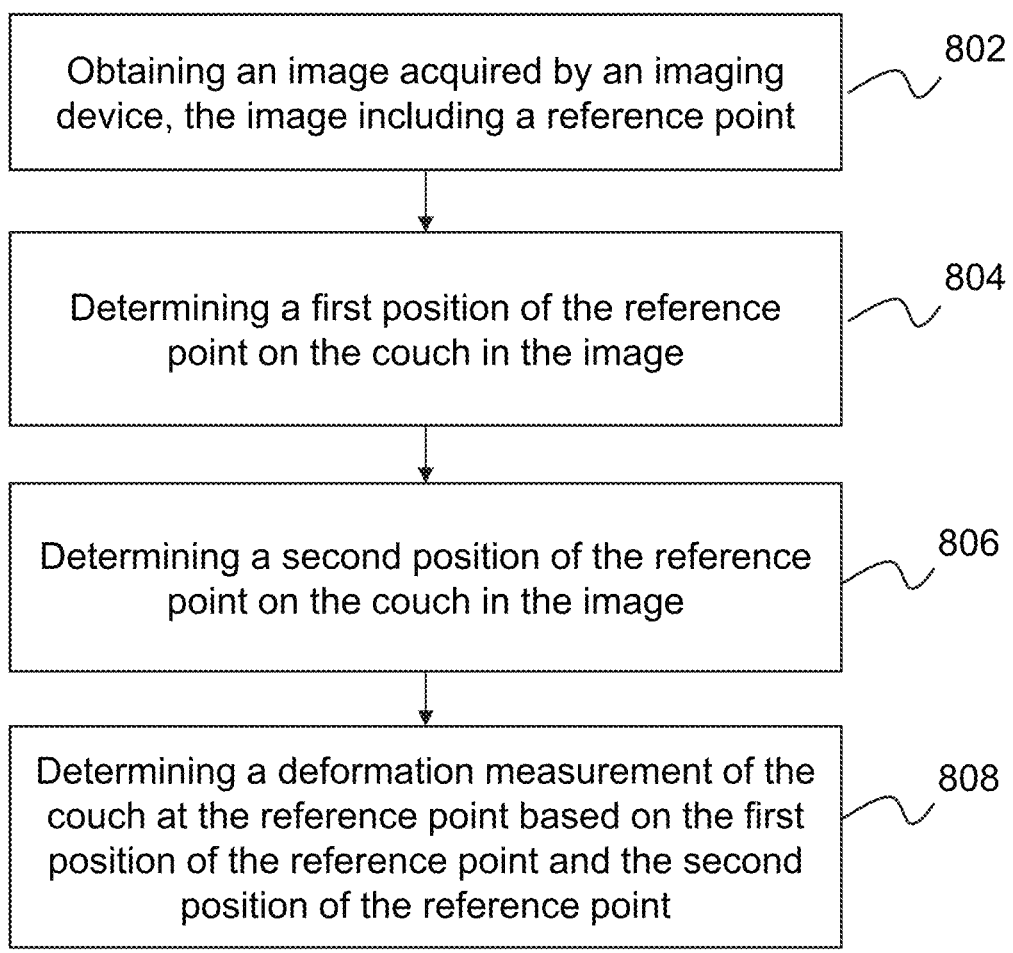
FIG. 8 is a flowchart illustrating an exemplary process for determining a deformation measurement of a couch at a reference point at an imaging position according to some embodiments of the present disclosure.

In some embodiments, the first deformation measurement of the couch at the reference point may be determined based an image relating to the reference point according to process 800 as described in FIG. 8. The image may be a CT image, a PET image, an MR image, or the like, or a combination thereof.

In some embodiments, the first deformation measurement of the couch at the reference point may be determined by using a measuring device (e.g., the first measuring device 980-1 and/or the second measuring device 980-2 as illustrated in FIG. 9). For example, a first actual distance (e.g., the distance h1 as shown in FIG. 9) from the reference point to the measuring device in an actual condition with a couch sag may be determined by using the measuring device. A first ideal distance (e.g., the distance h0 as shown in FIG. 9) from the reference point to the measuring device in an ideal condition without the couch sag may be determined based on a prior measurement. For example, information regarding the first ideal distance (e.g., the distance h0 as shown in FIG. 9) from the reference point to the measuring device may be retrieved from a storage (e.g., the storage 130, the storage module 508, etc.). The first deformation measurement (e.g., the sag S1 as shown in FIG. 9) may be determined based on a first difference between the first actual distance (e.g., the distance h1 as shown in FIG. 9) and the first ideal distance (e.g., the distance h0 as shown in FIG. 9) between the reference point and the measuring device. Further, the first deformation measurement (e.g., the first sag measurement) may be equal to a first difference between the first actual distance (e.g., the distance h1 as shown in FIG. 9) and the first ideal distance (e.g., the distance h0 as shown in FIG. 9) in the vertical direction (e.g., the Z direction in FIG. 9), respectively.

In 604, a second deformation measurement of the couch at the reference point may be determined. The second deformation measurement of the couch may correspond to a second working position of the couch. Operation 604 may be performed by the processing module 506. The second working position of the couch may be refer to a treatment position where a treatment device (e.g., the treatment device 940) is located. The reference point (e.g., point C as shown in FIG. 9) on the couch may be aligned with an isocenter of the treatment device (e.g., the isocenter 943 of the treatment device 940) in the vertical direction when the couch is at the second working position. The second deformation measurement of the couch at the reference point may relate to a position change of the reference point relative to an ideal condition without a couch sag (e.g., a couch sag caused by a loaded weight, couch sag caused by the weight of the couch). For example, the second deformation measurement of the couch may include a second sag measurement. In some embodiments, the second sag measurement of the couch at the reference point may relate to a position change of the reference point in a vertical direction (e.g., the sag S2 as shown in FIG. 9) when the couch sags caused by the subject loaded on the couch or the weight of the couch relative to an ideal condition when the couch does not sag.

In some embodiments, the second deformation measurement of the couch at the reference point may be determined based on the measuring device (e.g., the first measuring device 980-1 or the second measuring device 980-2 as illustrated in FIG. 9). For example, a second actual distance (e.g., the distance h2 as shown in FIG. 9) from the reference point to the measuring device in an actual condition with a couch sag may be determined by using the measuring device. A second ideal distance (e.g., the distance h0 as shown in FIG. 9) from the reference point to the measuring device in an ideal condition without a couch sag may be determined based on a prior measurement. For example, information regarding the second ideal distance (e.g., the distance h0 as shown in FIG. 9) from the reference point to the measuring device in an ideal condition without a couch sag may be retrieved from a storage (e.g., the storage 130, the storage module 508, etc.). The second deformation measurement (e.g., the sag S2 as shown in FIG. 9) may be determined based on a difference between the second actual distance (e.g., the distance h2 as shown in FIG. 9) and the second ideal distance (e.g., the distance h0 as shown in FIG. 9) from the reference point to the measuring device. Further, the second deformation measurement (e.g., the second sag measurement) may be equal to a difference between the second actual distance (e.g., the distance h2 as shown in FIG. 9) and the ideal distance (e.g., the distance h0 as shown in FIG. 9) in a vertical direction (e.g., the Z direction in FIG. 9), respectively.

In 606, a difference between the first deformation measurement and the second deformation measurement may be determined. Operation 606 may be performed by the processing module 506. In some embodiments, the difference between the first deformation measurement and the second deformation measurement may be determined based on a difference between the first actual distance (e.g., the distance h1 as shown in FIG. 9) from the reference point to the measuring device when the couch is at the first working position and the second actual distance (e.g., the distance h2 as shown in FIG. 9) from the reference point to the measuring device when the couch is at the second working position.

In 608, the second working position of the couch may be adjusted based on the difference between the first deformation measurement and the second deformation measurement. Operation 608 may be performed by the processing module 506. In some embodiments, the second working position of the couch may be adjusted to compensate the sagging of the couch at the reference point when the couch is at the second working position relative to the first working position, such that at least one part of the subject may be aligned with the isocenter of the treatment device (e.g., the RT device 240) for treatment. For example, when the couch moves from the first working position to the second working position (e.g., from the imaging device to the treatment device), the couch may deflect or sag. The deformation measurement of the couch at the second working position relative to the first working position may be related to the difference between the first deformation measurement of the couch and the second deformation measurement of the couch. The couch may be raised up or lowered down based on the difference between the first deformation measurement of the couch and the second deformation measurement of the couch. Thus, the at least one part of the subject may be aligned with the isocenter of the treatment device (e.g., the RT device 240) for treatment.

It should be noted that the above description is merely provided for the purposes of illustration, and not intended to limit the scope of the present disclosure. For persons having ordinary skills in the art, multiple variations or modifications may be made under the teachings of the present disclosure.

However, those variations and modifications do not depart from the scope of the present disclosure. For example, operations 602 and 604 may be unnecessary. Then, the first actual distance and the second actual distance in an actual condition with a couch sag from the reference point to the measuring device may be determined respectively. And, a deformation measurement of the couch at the second working position (e.g., a treatment position) relative to the first working position may be determined based on a difference between the first actual distance and the second actual distance. As another example, process 600 may include obtaining movement data relating to the couch acquired by the measuring device.

FIG. 7 is a flowchart illustrating an exemplary process 700 for determining a deformation measurement of a couch at a treatment position relative to an imaging position according to some embodiments of the present disclosure. In some embodiments, one or more operations of process 700 illustrated in FIG. 7 may be implemented in the diagnosis and treatment system 100 illustrated in FIG. 1. For example, the process 700 illustrated in FIG. 7 may be stored in the storage 130 in the form of instructions, and invoked and/or executed by the processing device 120 (e.g., the processor 310 of the computing device 300 as illustrated in FIG. 4, the GPU 430 or CPU 440 of the mobile device 400 as illustrated in FIG. 4).

In 702, a displacement measurement of a reference point on a couch between a first working position and a second working position may be determined by using at least one measuring device. Operation 702 may be performed by the processing module 506. As used herein, the displacement measurement of the reference point on the couch may refer to a location change of the reference point in the space accommodating a medical device (e.g., the RT-CT apparatus 200) when the couch moves from the first working position to the second working position. The medical device (e.g., the RT-CT apparatus 200) may include an imaging device (e.g., the CT device 220) and a treatment device (e.g., the RT device 240). The first working position of the couch may refer to an imaging position where the imaging device (e.g., the CT device 220) is located. The second working position of the couch may refer to a treatment position where the treatment device (e.g., the RT device 240) is located. The reference point on the couch may be determined based on an isocenter of the imaging device (e.g., the isocenter 223 of the CT device 220). For example, the reference point may be a point on the couch which is aligned with the isocenter of the imaging device (e.g., the isocenter 223 of the CT device 220) in the vertical direction when the couch is at the first working position.

In some embodiments, the displacement measurement of the reference point on the couch may be acquired from the at least one measuring device directly. In some embodiments, the displacement measurement of the reference point on the couch may be determined based on other static data relating to the position of the reference point (e.g., a distance of the reference point on the couch to a measuring device, an angle between the reference point on the couch and the measuring device) by the processing module 506. For example, the displacement of the reference point on the couch may be determined based on a laser triangulation algorithm. Furthermore, the at least one measuring device (e.g., a laser rangefinder) may emit a laser to the couch, and the couch may reflect the laser to the at least one measuring device (e.g., a laser interferometer). The displacement measurement of the reference point on the couch may be determined based on the reflected laser and the emitting laser by using the laser triangulation algorithm. As still an example, the displacement measurement of the reference point on the couch may be determined based on images relating to the reference point acquired by the at least one measuring device (e.g., an optical detector). Further, the at least one measuring device (e.g., an optical detector) may determine the displacement measurement of the reference point based on the images via, for example, an edge detection algorithm, a center detecting algorithm, etc.

In 704, a deformation measurement of the couch at the reference point may be determined based on the displacement measurement of the reference point on the couch. The deformation measurement of the couch at the reference point may correspond to the second working position of the couch. Operation 704 may be performed by the processing module 506. The deformation measurement (e.g., a sag measurement) of the couch at the reference point may relate to a component in a vertical direction (e.g., the Z direction as shown in FIG. 2) of the displacement measurement of the couch at the reference point.

In 706, the second working position of the couch may be adjusted based on the deformation measurement of the couch at the reference point. Operation 706 may be performed by the processing module 506. In some embodiments, the second working position of the couch may be adjusted to compensate the sagging of the couch at the reference point when the couch is at the second working position relative to the first working position, such that at least one part of the subject may be coincided with the isocenter of the treatment device (e.g., the RT device 240) for treatment. For example, when the couch moves from the first working position to the second working position (e.g., from the imaging device to the treatment device), the couch may deflect or sag with the deformation measurement determined in 704. The couch may be raised up or lowered down based on the deformation measurement. Thus, the at least one part of the subject may be coincided with the isocenter of the treatment device (e.g., the RT device 240) for treatment.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 700 may include obtaining static data relating to the position of the couch acquired by the measuring device. As another example, operation 706 may be unnecessary.

FIG. 8 is a flowchart illustrating an exemplary process 800 for determining a deformation measurement of a couch at a reference point at an imaging position according to some embodiments of the present disclosure. In some embodiments, one or more operations of process 800 illustrated in FIG. 8 may be implemented in the diagnosis and treatment system 100 illustrated in FIG. 1. For example, the process 800 illustrated in FIG. 8 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operation 602 may be performed according to process 800.

In 802, an image including a reference point acquired by an imaging device may be obtained. Operation 802 may be performed by the acquisition module 502. The imaging device may include a medical imaging device, such as a CT device, a CBCT device, a PET device, an MR device, or the like, or a combination thereof. The image may be acquired from the imaging device (e.g., the CT device 220), the storage 130, the terminal 140, or any other storage. The reference point may be a point on the couch aligning with an isocenter of the imaging device (e.g., the isocenter of the CT device 220) in the vertical direction. The reference point may be represented in the image as a point which may be identified from the image.

In 804, a first position of the reference point may be determined based on the image. Operation 804 may be performed by the processing module 506. In some embodiments, a coordinate system may be applied to the image. The coordinate system may be a 2D or a 3D coordinate system. Further, the coordinate system applied to the image may have a coordinate origin at the center of the image. The first position of the reference point may be represented by first coordinates corresponding to the coordinate system. The first coordinates of the couch at the reference point may be obtained from the coordinate system applied to the image. As used herein, the first coordinates of the reference point may refer to an actual position of the reference point in the coordinate system when the couch sags. The couch sag may be caused by a loaded weight and/or the weight of the couch.

In 806, a second position of the reference point may be determined based on the image. The second position of the reference point may be represented by second coordinates corresponding to the coordinate system. The second coordinates of the reference point may refer to an ideal position of the reference point in the coordinate system applied to the image when the couch does not sag.

In some embodiments, the second coordinates may be determined based on one or more of the following operations. The coordinates of an isocenter of the imaging device (e.g., the isocenter 223 of the CT device 220) may be determined in the image. The coordinates of the isocenter of the imaging device (e.g., the isocenter 223 of the CT device 220) may be illustrated in the coordinate system applied to the image. The isocenter of the imaging device may correspond to a scanning center of the imaging device, which when illustrated in the image, corresponds to a center of the image. For example, the coordinates of the isocenter of the imaging device may be equal to the coordinates of the scanning center of the imaging device. As another example, the coordinates of the isocenter of the imaging device may be determined based on the coordinates of the scanning center of the imaging device and a displacement of the isocenter of the imaging device or a displacement of the scanning center of the imaging device. The displacement of the isocenter of the imaging device or the displacement of the scanning center of the imaging device may be configured by a user of the diagnosis and treatment system 100. Then, the second coordinates of the reference point may be determined based on the coordinate of the isocenter of the imaging device and a position of the table top of couch in the image in an ideal condition when the couch does not sag. Information regarding the position of the table top of the couch in the image in an ideal condition when couch does not sag may be obtained from, e.g., a prior measurement. For example, the information regarding the position of the table top of the couch in the image in an ideal condition may be retrieved from a storage (e.g., the storage 130, the storage module 508, etc.).

In some embodiments, the second position of the reference point may be stored in a storage (e.g., the storage 130, the storage module 508, etc.). The second coordinates of the reference point may be retrieved from the storage for future use.

In 808, a deformation measurement of the couch at the reference point may be determined based on the first position of the reference point and the second position of the reference point. Operation 808 may be performed by the processing module 506. The deformation measurement of the couch at the reference point when the couch is at the imaging position may be determined based on a difference between the first position and the second position. Further, the deformation measurement of the couch at the reference point may be determined based on a difference between the first coordinates of the reference point and the second coordinates of the reference point in the vertical direction.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 802 may be unnecessary. As another example, operations 802 and 804 may be performed simultaneously.

Example 1

FIG. 9 is a schematic diagram illustrating for determining a sag measurement at a treatment position relative to an imaging position according to some embodiments of the present disclosure. As shown in FIG. 9, the IGRT apparatus 110 may include an imaging device 920, a treatment device 940, a couch 960, and one or more measuring devices (e.g., a first measuring device 980-1 and a second measuring device 980-2). The first measuring device 980-1 and the second measuring device 980-2 may be aligned with an isocenter 923 of the imaging device 920 and an isocenter 943 of the treatment device 940, respectively in a vertical direction. The vertical direction may be the Z axial direction as shown in FIG. 9.

When the couch 960 is loaded with a subject, the couch 960 may generate a first sag at point C. Point C may be aligned to the isocenter 923 of the imaging device 920 in a vertical direction (e.g., the Z axial direction) when the couch is at an imaging position where the imaging device 920 is located. A first sag measurement (i.e., the sag S1) of the couch 960 at point C may be determined based on a distance from point C to the first measuring device 980-1 in the Z axial direction (i.e., the distance h1) and a distance from point D to the first measuring device 980-1 in the Z axial direction (i.e., the distance h0). Further, the first sag measurement may be equal to a difference between the distance h0 and the distance h1. The height of point D may correspond to an ideal height of point C when the couch does not sag at the imaging position. When the couch 960 (i.e., the couch 960') is moved to a treatment position where the treatment device 940 is located, the couch 960' may generate a second sag at point C' corresponding to point C. Point C' may be aligned to the isocenter 943 of the treatment device 940 in the vertical direction (e.g., the Z axial direction) when the couch is at the treatment position. A second sag measurement (i.e., the sag S2) of the couch 960' at point C' may be determined based on a distance from point C' to the a second measuring device 980-2 in the Z axial direction (i.e., the distance h2) and a distance from point D' to the second measuring device 980-2 in the Z axial direction (i.e., the distance h0). Further, the second sag measurement may be equal to a difference between the distance h0 and the distance h2. The height of point D' may correspond to an ideal height of point C' when the couch does not sag at the treatment position. Then, a sag measurement of the couch at point C' may be determined based on a difference between the first sag measurement and the second sag measurement. The sag measurement of the couch at point C' determined based on the difference between the first sag measurement and the second sag measurement may be a sag of the couch 960' at point C' relative to the imaging position.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the first measuring device 980-1 and the second measuring device 980-2 may be not aligned with the isocenter 923 of the imaging device 920 and/or the isocenter 943 of the treatment device 940, respectively in the vertical direction. As another example, the sag measurement of the couch at point C' may be determined based on a difference between the distance h1 and the distance h2 directly.

Example 2

Figure 10:
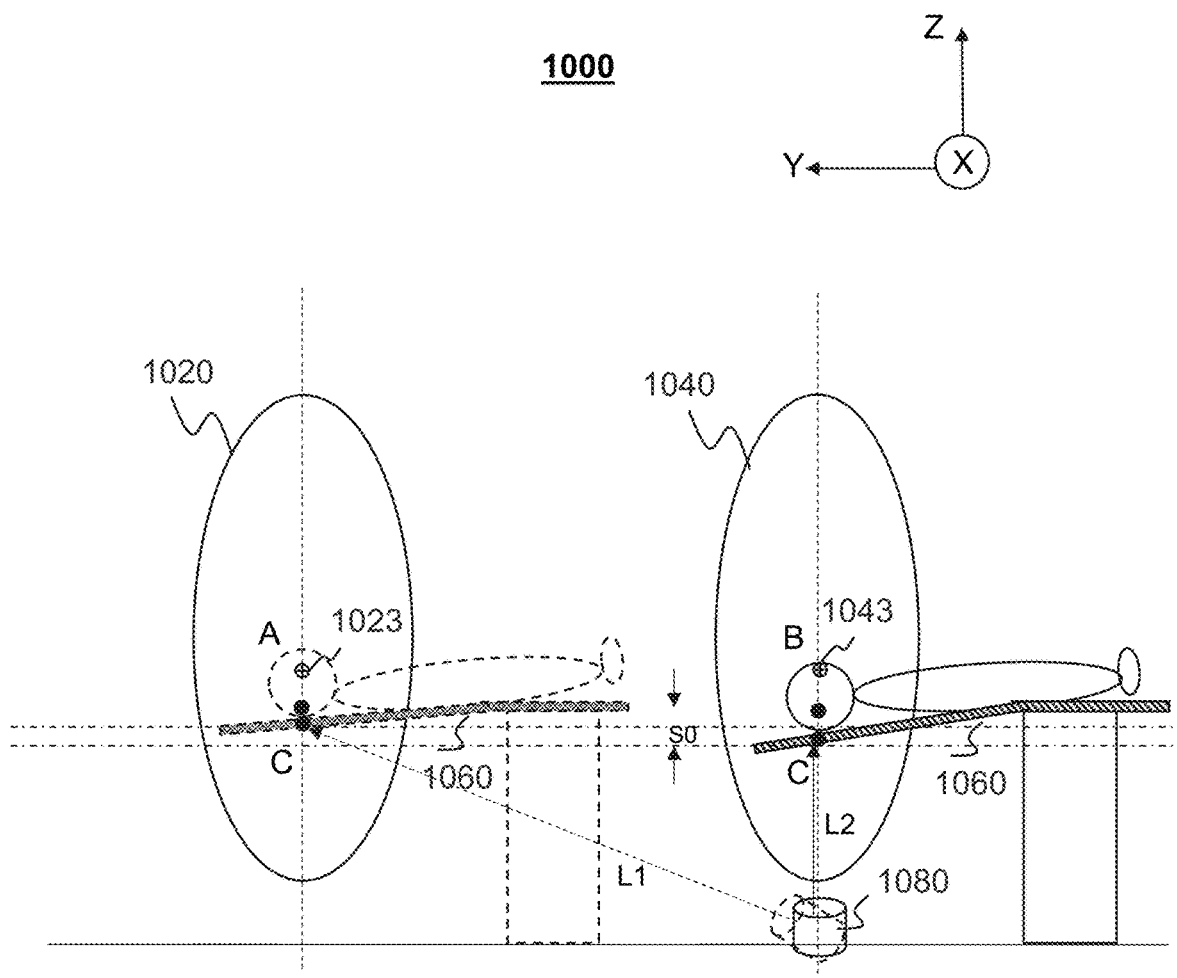
FIG. 10 is a schematic diagram illustrating an example for determining a sag measurement for an exemplary IGRT apparatus according to some embodiments of the present disclosure.

FIG. 10 is a schematic diagram illustrating an example for determining a sag measurement for an exemplary IGRT apparatus 1000 according to some embodiments of the present disclosure. As shown, the IGRT apparatus 1000 may include a CT device 1020, a radio therapy (RT) device 1040, a couch 1060, and an electromagnetic induction apparatus 1080. The CT device 1020 and the RT device 1040 may be located at different positions in the space accommodating the IGRT apparatus 1000. The CT device 1020 and the RT device 1040 may share the same couch 1060. The couch 1060 may move along various directions. For example, the couch 1060 may extend along the longitudinal direction of the couch 1060. As another example, the couch 1060 may be moved from the position where the CT device 1020 is located to the position where the RT device 1040 is located. The electromagnetic induction apparatus 1080 may be aligned with an isocenter 1043 of the RT device 1040 in a vertical direction. The vertical direction may be the Z axial direction as shown in FIG. 10. The electromagnetic induction apparatus 1080 may be used to determine a displacement between, for example, the electromagnetic induction apparatus 1080 and a specified position of the couch (e.g., point C).

When the couch 1060 is loaded with a subject and is moved from an imaging position (i.e., the position where the CT 1020 device is located) to a treatment position (i.e., the position where the RT device 1040 is located), the couch may generate a sag at point C' at the treatment position relative to the imaging position. The sag measurement S0 of the couch at point C' may relate to a displacement of point C when the couch 1060 is moved from the imaging position to the treatment position (e.g., the position of the couch 1060' is located). Further, the sag measurement S0 of the couch at point C' may be equal to a magnitude of the displacement of point C in the vertical direction (i.e., the Z axial direction).

Example 3

Figure 11:
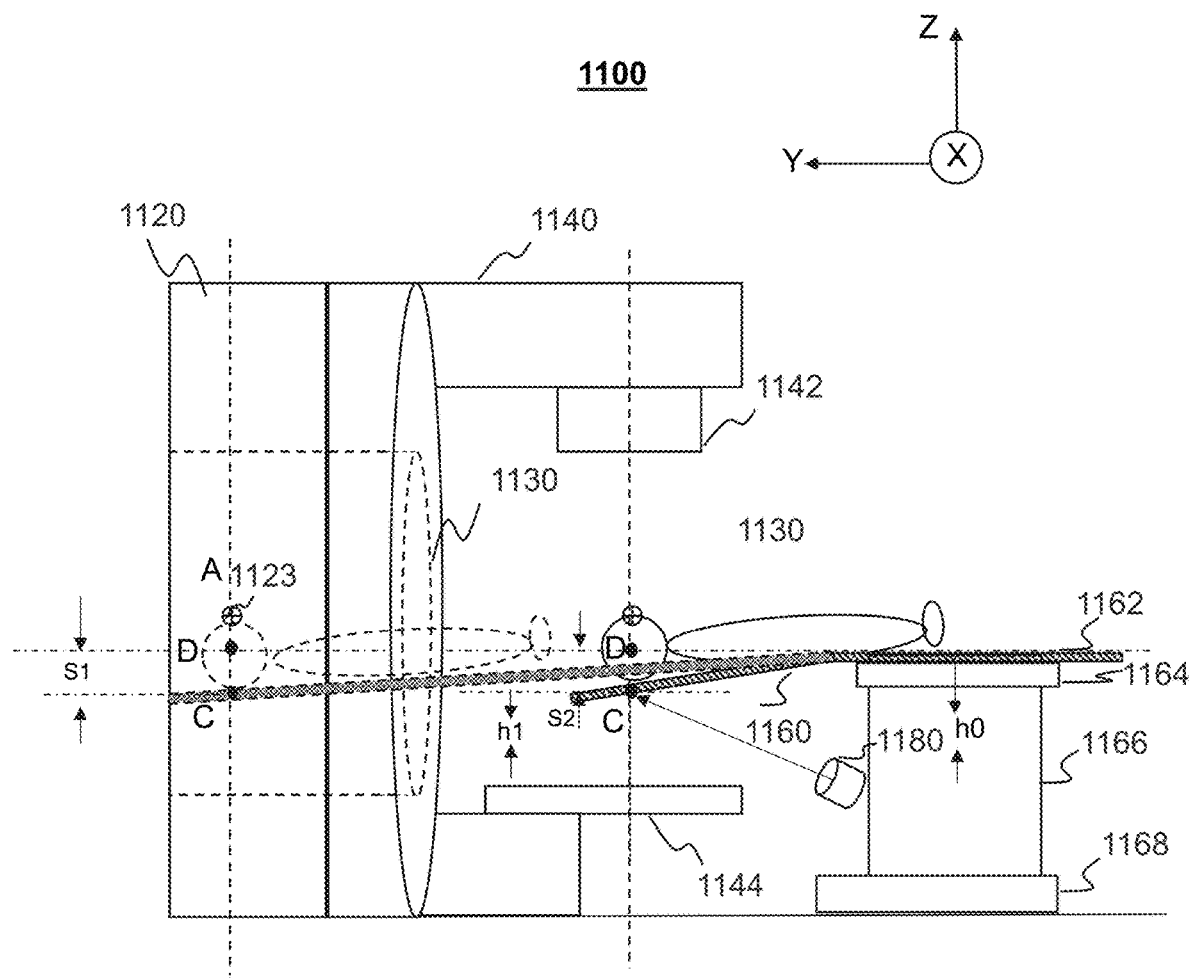
FIG. 11 is a schematic diagram illustrating an example for determining a sag measurement for an exemplary IGRT apparatus according to some embodiments of the present disclosure.

FIG. 11 is a schematic diagram illustrating an example for determining a sag measurement for an exemplary IGRT apparatus 1100 according to some embodiments of the present disclosure. As shown, the IGRT apparatus 1100 may include a CT device 1120, a RT device 1140, a couch 1160, and a laser rangefinder 1180. The CT device 1120 may be coupled to the RT device 1140. The CT device 1120 and the RT device 1140 may share a same bore 1130 and/or the same couch (e.g., the couch 1160). The RT device 1140 may include a radiation source 1142 and a detector 1144. The radiation source 1142 may emit radiation beams to be used for treatment and/or imaging. The detector 1144 may detect radiation beams emitted by the radiation source 1142. The couch 1160 may be moved in the bore 1130 and transfer a subject to be imaged to the CT device 1120. The couch 1160 may further include a table top 1162, a first supporting assembly 1164, a second supporting assembly 1166, and a base 1168. The first supporting assembly 1164 may include a first movement component (not shown) configured to move the table top 1162 along the longitudinal direction (i.e., the Y axial direction). The second supporting assembly 1166 may include a second movement component (not shown) configured to move the table top 1162 in the vertical direction (i.e., the Z axial direction). The base 1168 may include a third movement component (not shown) configured to rotate the couch 1160. The laser rangefinder 1180 may be used to determine a distance between the laser rangefinder 1180 and a specified position of the couch (e.g., point C). The laser rangefinder 1180 may be mounted on the second supporting assembly 1166 of the couch 1160. The laser rangefinder 1180 may be configured to emit electromagnetic waves along various directions and receive electromagnetic waves reflected by an object (e.g., the couch 1160). More descriptions of at least one portion of the IGRT apparatus (e.g., the CT device 1120, the radiation therapy (RT) device 1140, the couch 1160) may be found in US Publication No. 20170189719 entitled "RADIATION THERAPY POSITIONING SYSTEM.", US Publication No. 20170189720 entitled "RADIATION THERAPY SYSTEM.", and/or US Publication No. 20170189724 entitled "RADIATION THERAPY SYSTEM.", the contents of which are hereby incorporated by reference.

When the couch 1160 is loaded with a subject to be imaged, the table top 1162 may be extended along the longitudinal direction of the couch 1160 (i.e., the Y axial direction as shown in FIG. 11). The table top 1162 may generate a first sag at point C under the loaded subject and/or the weight of the couch 1160. The first sag measurement S1 may be determined based on a CT image relating to the subject and point C according to process 800 as illustrated in FIG. 8. When the table top 1162 is extended to a treatment position where the RT device 1140 is located, the table top 1162 may generate a second sag at point C' corresponding to point C at the treatment position. The second sag measurement at point C' may be determined based on the laser rangefinder 1180 or the RT device 1140. For example, the laser rangefinder 1180 then may be configured to determine a distance between the laser rangefinder 1180 to point C' as described above. Then the second sag measurement S2 may be equal to a difference between the distance h0 and the distance h1. The height of point D' (i.e. distance h0) from the ground may correspond to an ideal height of point C' when the table top 1162 does not sag at the treatment position. As another example, the detector 1144 may be used to detect radiation beams and generate projection data based on the detected radiation beams. The projection data may be used to generate a radiation image relating to point C'. The second sag measurement S2 may be determined based on the radiation image relating to point C' according to process 800 as illustrated in FIG. 8. Then, a sag measurement of the couch 1160 at point C' may be determined based on a difference between the first sag measurement S1 and the second sag measurement S2. The sag measurement of the couch at point C' determined based on the difference between the first sag measurement S1 and the second sag measurement S2 may be a sag of the couch 1160 at point C' when the couch 1160 is extended from the imaging position to the treatment position.

Example 4

Figure 12:
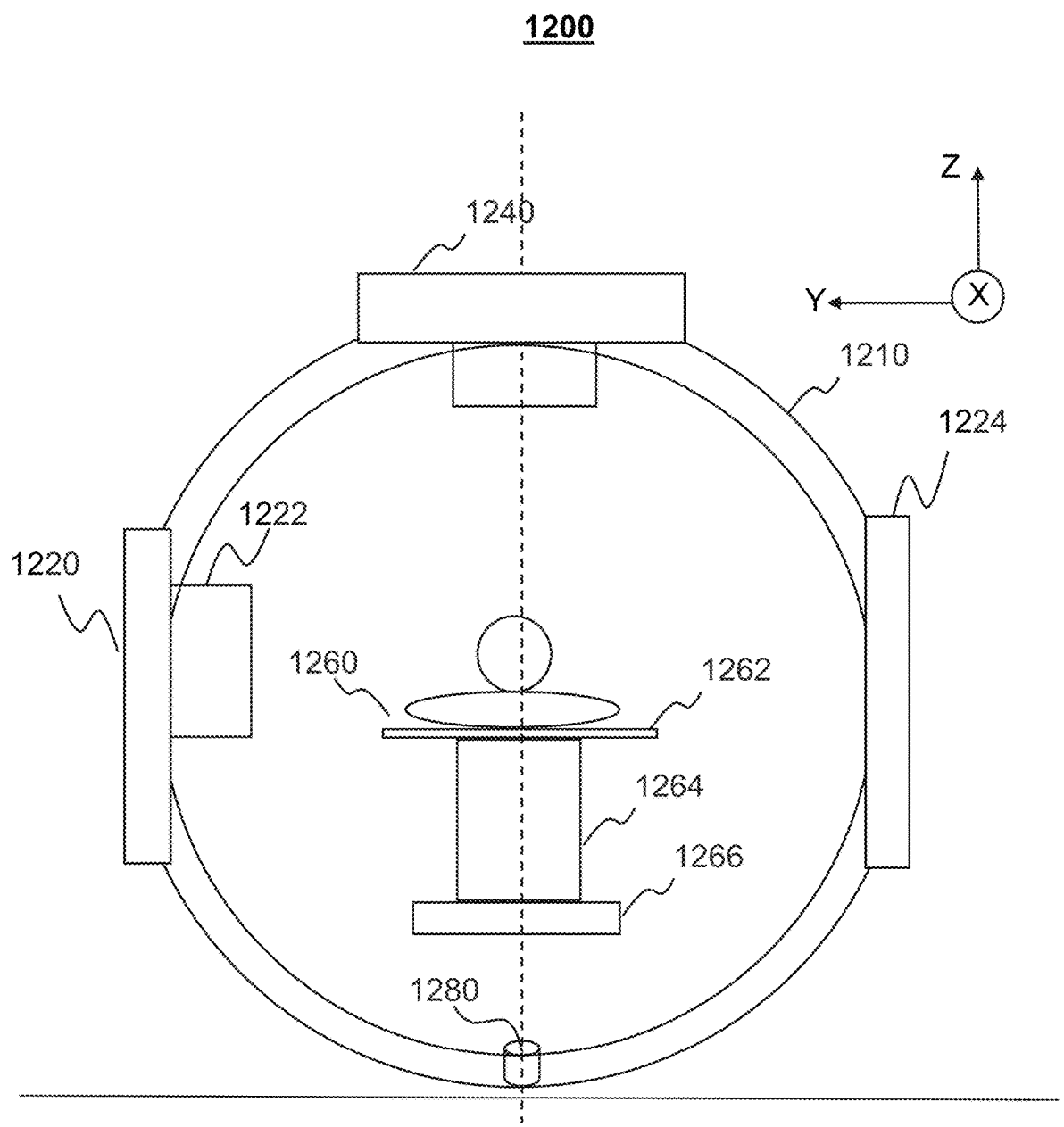
FIG. 12 is a schematic diagram illustrating an example for determining a sag measurement for an exemplary IGRT apparatus according to some embodiments of the present disclosure.

FIG. 12 is a schematic diagram illustrating an example for determining a sag measurement for an exemplary IGRT apparatus 1200 according to some embodiments of the present disclosure. As shown, the IGRT apparatus 1200 may include a gantry 1210, a CT device 1220, a radio therapy (RT) device 1240, a couch 1260, and an optical detector apparatus 1280. The gantry 1210 may be configured to support at least one portion of the IGRT apparatus 1200, such as the CT device 1220, the RT device 1240, etc. The CT device 1220 may include a radiation source 1222 and a detector 1224. The radiation source 1222 may be mounted on one side of the gantry 1210 and have an angle of 90 degree with the RT device 1240. The detector 1224 may be mounted on another side of the gantry 1210 opposite the radiation source 1222. The couch 1260 may be extended along the longitudinal direction of the couch 1260 (e.g., the X axial direction as shown in FIG. 12) and transfer a subject to a detecting region defined by the CT device 1220 and/or the RT device 1240. The couch 1260 may further include a table top 1262, at least one supporting assembly 1264, and a base 1266. The couch 1260 may further include at least one optical marker (not shown). The optical marker may be imaged by the optical detector apparatus 1280. The optical detector apparatus 1280 may be used to determine a distance between, for example the optical detector apparatus 1280 and a specified position of the couch (e.g., point C). For example, the optical detector apparatus 1280 may be configured to generate an optical image relating to a marker at point C. The distance between the optical detector apparatus 1280 and point C may be determined based on the optical image relating to the marker. The optical detector apparatus 1280 include an optical sensor array including a plurality of optical sensors (e.g., CCD). The optical detector apparatus 1280 may be located under the RT device 1240. More descriptions of at least one portion of the IGRT apparatus 1200 (e.g., the CT device 1220, the RT device 1240, the couch 1260) may be found in US Publication No. 20170189719 entitled "RADIATION THERAPY POSITIONING SYSTEM.", US Publication No. 20170189720 entitled "RADIATION THERAPY SYSTEM.", and/or US Publication No. 20170189724 entitled "RADIATION THERAPY SYSTEM.", the contents of which are hereby incorporated by reference.

When the couch 1260 is loaded a subject at an imaging position (i.e., the detecting position), the couch 1260 may generate a first sag. The first sag measurement may be determined by using the optical detector apparatus 1280. When the subject is treated, the couch 1260 may generate a second sag. The second sag measurement may be determined by using the optical detector apparatus 1280. The sag measurement of the couch 1260 at a treatment position relative to the imaging position may be determined based on difference between the first sag measurement and the second sag measurement.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    a computer-readable storage medium storing executable instructions, and
    at least one processor in communication with the computer-readable storage medium, when executing the executable instructions, causing the system to implement a method, comprising:
        determining first position data of a reference point at a couch of a medical device when a subject is lying on the couch, the first position data corresponding to a first working position of the couch, wherein the reference point is located at a fixed position on the couch and moves with a motion of the couch;
        determining second position data of the reference point when the subject is lying on the couch, the second position data corresponding to a second working position of the couch, wherein the medical device includes a first modality device located at the first working position and a second modality device located at the second working position, the first modality device is different from the second modality device, the reference point moves between the first modality device and the second modality device; and
        causing an adjustment of one of the first working position or the second working position of the couch based on a difference between the first position data and the second position data.

2. The system of claim 1, wherein the first working position of the couch is related to an imaging position, the first modality device includes a computed tomography (CT) device, and the second working position of the couch is related to a treatment position, the second modality device includes a radio therapy (RT) device.

3. The system of claim 1, wherein the medical device includes an imaging device, and the determining first position data of the reference point at the couch of the medical device when the subject is lying on the couch includes:
    obtaining an image acquired by the imaging device, the image acquired by the imaging device including the reference point, the reference point aligning to an isocenter of the imaging device; and
    determining the first position data of the reference point based on the image acquired by the imaging device.

4. The system of claim 1, wherein the determining first position data of the reference point at the couch of the medical device when the subject is lying on the couch includes:
    determining the first position data of the reference point based on at least one first measuring device.

5. The system of claim 4, wherein the determining the first position data of the reference point based on the at least one first measuring device includes:
    determining a distance from the reference point on the couch at the first working position to the at least one first measuring device by using the at least one first measuring device, the reference point aligning to an isocenter of an imaging device of the medical device; and determining the first position data based on the distance from the reference point on the couch at the first working position to the at least one first measuring device.

6. The system of claim 5, wherein the at least one first measuring device aligns to the isocenter of the imaging device of the medical device.

7. The system of claim 4, wherein the at least one first measuring device includes at least one of an optical detector apparatus, a rangefinder apparatus, or an electromagnetic induction apparatus, and the at least one first measuring device or at least one second measuring device does not move with the motion of the couch.

8. The system of claim 4, wherein the determining second position data of the reference point when the subject is lying on the couch includes:

determining the second position data of the reference point based on the at least one first measuring device when the couch is moved to the second working position where a RT device is located.

9. The system of claim 8, wherein the determining the second position data of the reference point based on the at least one first measuring device includes:

determining a distance from the reference point on the couch at the second working position to the at least one first measuring device by using the at least one first measuring device, the reference point aligning to an isocenter of a treatment device of the medical device; and determining the second position data of the reference point based on the distance from the reference point on the couch at the second working position to the at least one first measuring device.

10. The system of claim 4, wherein the determining second position data of the reference point when the subject is lying on the couch includes:

determining the second position data of the reference point based on at least one second measuring device when the couch is moved to the second working position where a RT device is located.

11. The system of claim 10, wherein the determining the second position data of the reference point based on the at least one second measuring device includes:

determining a distance from the reference point on the couch at the second working position to the at least one second measuring device by using the at least one second measuring device, the reference point aligning to an isocenter of a treatment device of the medical device; and determining the second position data of the reference point based on the distance from the reference point on the couch at the second working position to the at least one second measuring device.

12. The system of claim 11, wherein the at least one second measuring device aligns to the isocenter of the treatment device of the medical device.

13. The system of claim 10, wherein the at least one second measuring device includes at least one of an optical detector apparatus, a rangefinder apparatus, or an electromagnetic induction apparatus.

14. The system of claim 13, wherein the optical detector apparatus includes at least one charge-coupled device (CCD).

15. The system of claim 13, wherein the electromagnetic induction apparatus includes a magnetic induction coil, an electromagnetic launcher (EML), and an electromagnetic receiver, the magnetic induction coil being coupled to the couch.

16. The system of claim 13, wherein the rangefinder apparatus includes at least one of an ultrasonic rangefinder, a laser rangefinder, or a radar rangefinder.

17. The system of claim 1, wherein the determining second position data of the reference point when the subject is lying on the couch includes:

obtaining an image acquired by a detector of a treatment device of the medical device, wherein the detector is aligned with or angled from a treatment radiation source, the image acquired by the detector of the treatment device includes the reference point, the reference point is aligned to an isocenter of the treatment device; and determining the second position data of the reference point at the second working position based on the image acquired by the treatment device.

18. The system of claim 1, wherein the determining second position data of the reference point when the subject is lying on the couch includes:

determining a deformation measurement of the couch at the reference point at the second working position relative to the first working position based on the difference between the first position data and the second position data; and causing an adjustment of the second working position of the couch based on the deformation measurement of the couch.

19. A system, comprising:

at least one storage device storing executable instructions, and at least one processor in communication with the at least one storage device, when executing the executable instructions, causing the system to:

determine a reference point at a couch when a subject is lying on the couch, the reference point aligning to an isocenter of a first medical device when the couch is located at a first working position and aligning to an isocenter of a second medical device when the couch is located at a second working position when the subject is lying on the couch, wherein the reference point is located at a fixed position on the couch and moves with a motion of the couch;

determine a deformation measurement of the couch at the reference point at the second working position relative to the first working position, wherein the medical devices includes a first modality device located at the first working position and a second modality device located at the second working position, the first modality device is different from the second modality device, the reference point moves between the first modality device and the second modality device; and cause an adjustment of one of the first working position and the second working position of the couch based on the deformation measurement.

20. A method implemented on a computing device having at least one processor, at least one computer-readable storage medium, and a communication port connected to a medical device including a couch, the method comprising:

determining first position data of a reference point at the couch of the medical device when a subject is lying on the couch, the first position data corresponding to a first working position of the couch, wherein the reference point is located at a fixed position on the couch and moves with a motion of the couch;

determining second position data of the reference point when the subject is lying on the couch, the second position data corresponding to a second working position of the couch, wherein the medical device includes a first modality device located at the first working position and a second modality device located at the second working position, the first modality device is different from the second modality device; the reference point moves between the first modality device and the second modality device; and causing an adjustment of one of the first working position or the second working position of the couch based on a difference between the first position data and the second position data.

* * * * *